United States Patent
Shong et al.

(10) Patent No.: US 10,233,382 B2
(45) Date of Patent: Mar. 19, 2019

(54) METHOD OF USING MULTICARBOXYLATE COMPOSITIONS IN ENHANCED OIL RECOVERY

(71) Applicant: Chevron U.S.A. Inc., San Ramon, CA (US)

(72) Inventors: Robert George Shong, Houston, TX (US); Varadarajan Dwarakanath, Houston, TX (US); Gregory A. Winslow, Houston, TX (US); Sophany Thach, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 15/471,255

(22) Filed: Mar. 28, 2017

(65) Prior Publication Data

US 2017/0198202 A1    Jul. 13, 2017

Related U.S. Application Data

(62) Division of application No. 14/668,147, filed on Mar. 25, 2015.

(51) Int. Cl.
| | | |
|---|---|---|
| C09K 8/584 | (2006.01) | |
| E21B 43/16 | (2006.01) | |
| C09K 8/588 | (2006.01) | |
| C07C 59/305 | (2006.01) | |

(52) U.S. Cl.
CPC ............ *C09K 8/584* (2013.01); *C07C 59/305* (2013.01); *C09K 8/588* (2013.01); *E21B 43/16* (2013.01)

(58) Field of Classification Search
None
See application file for complete search history.

(56) References Cited

U.S. PATENT DOCUMENTS

| | | |
|---|---|---|
| 3,308,067 A | 3/1967 | Diehl |
| 3,723,322 A | 3/1973 | Diehl |
| 4,144,226 A | 3/1979 | Crutchfield et al. |
| 4,556,495 A | 12/1985 | Shaw |
| 5,233,087 A | 8/1993 | Cripe |

(Continued)

FOREIGN PATENT DOCUMENTS

| | | |
|---|---|---|
| WO | 95/07334 | 3/1995 |
| WO | 2013/148712 | 10/2013 |

*Primary Examiner* — Jeffrey D Washville
(74) *Attorney, Agent, or Firm* — Karen R. DiDomenicis

(57) ABSTRACT

The present disclosure relates to the use of a multicarboxylate, such as an alkyl alkoxy dicarboxylate, in enhanced oil recovery processes. A specific embodiment relates to the use of an aqueous stream including a compound having the chemical formula: $R_1$—$R_2$—$R_3$, wherein $R_1$ comprises a branched or unbranched, saturated or unsaturated, cyclic or non-cyclic, hydrophobic carbon chain having 7-150 carbon atoms; an oxygen atom linking $R_1$ and $R_2$; $R_2$ comprises an alkoxylated chain comprising ethylene oxide, propylene oxide, butylene oxide, or a combination thereof; and $R_3$ comprises a branched or unbranched hydrocarbon chain comprising 2-12 carbon atoms and 2-5 —COOH or —COOM groups wherein M is a monovalent, divalent, or trivalent cation.

10 Claims, 1 Drawing Sheet

(56) References Cited

U.S. PATENT DOCUMENTS

| | | | |
|---|---|---|---|
| 5,739,092 A | 4/1998 | Ofosu-Asante | |
| 6,269,881 B1 | 8/2001 | Chou et al. | |
| 6,365,774 B1 | 4/2002 | O'Lenick, Jr. | |
| 7,770,641 B2 | 8/2010 | Dwarakanath et al. | |
| 8,841,241 B2 | 9/2014 | Weerasooriya et al. | |
| 2011/0281779 A1 | 11/2011 | Weerasooriya et al. | |
| 2012/0101010 A1 | 4/2012 | Weerasooriya et al. | |
| 2012/0241220 A1* | 9/2012 | Quintero ................. | C09K 8/34 175/65 |
| 2013/0252855 A1 | 9/2013 | Weerasooriya et al. | |
| 2014/0262286 A1 | 9/2014 | Dwarakanath et al. | |
| 2015/0048007 A1 | 2/2015 | Weerasooriya et al. | |

\* cited by examiner

METHOD OF USING MULTICARBOXYLATE COMPOSITIONS IN ENHANCED OIL RECOVERY

CROSS-REFERENCE TO RELATED APPLICATIONS

The present disclosure is related to, and claims priority from U.S. application Ser. No. 14/668,147, Mar. 26, 2015, which claims priority from U.S. Provisional Application No. 61/970,633, with a filing date of Mar. 26, 2014; U.S. Provisional Application No. 61/970,578, with a filing date of Mar. 26, 2014, and U.S. Provisional Application No. 62/021,764, with a filing date of Jul. 8, 2014. These disclosures are incorporated herein by reference for all purposes.

TECHNICAL FIELD

The present disclosure generally relates to a multicarboxylate, such as an alkyl alkoxy dicarboxylate or an alkylaryl carboxylate and a method of using the multicarboxylate in enhanced oil recovery (EOR) applications.

BACKGROUND

Alkoxy carboxylates have been used as surfactant additives in a variety of settings, such as in shampoos, laundry detergents, and liquid dish washing compositions. These carboxylic acid compositions have additional potential application as oil additives, such as in marine engines, and in situations where water emulsion formation can occur. They may also have cosmetic applications in combination with Guerbet esters which are highly valued cosmetic esters for their exceptional emolliency properties in skin and body creams. Additionally, alkoxy carboxylates are used in tertiary oil recovery processes. However, all such alkoxy carboxylates have only included one carboxylate group.

Reservoir systems, such as petroleum reservoirs, typically contain fluids such as water and a mixture of hydrocarbons such as oil and gas. To remove ("produce") the hydrocarbons from the reservoir, different mechanisms can be utilized such as primary, secondary or tertiary recovery processes.

In a primary recovery process, hydrocarbons are displaced from a reservoir through the high natural differential pressure between the reservoir and the bottom hole pressure within a wellbore. The reservoir's energy and natural forces drive the hydrocarbons contained in the reservoir into the production well and up to the surface. Artificial lift systems, such as sucker rod pumps, electrical submersible pumps or gas-lift systems, are often implemented in the primary production stage to reduce the bottom hole pressure within the well. Such systems increase the differential pressure between the reservoir and the wellbore intake; thus, increasing hydrocarbon production. However, even with use of such artificial lift systems only a small fraction of the original-oil-in-place (OOIP) is typically recovered using primary recovery processes as the reservoir pressure, and the differential pressure between the reservoir and the wellbore intake declines over time due to production. For example, typically only about 10-20% of the OOIP can be produced before primary recovery reaches its limit, either when the reservoir pressure is so low that the production rates are not economical or when the proportions of gas or water in the production stream are too high.

In order to increase the production life of the reservoir, secondary or tertiary recovery processes can be used. Secondary recovery processes include water or gas well injection, while tertiary methods are based on injecting additional chemical compounds into the well, such as surfactants and polymers. Typically in these processes, fluids are injected into the reservoir to maintain reservoir pressure and drive the hydrocarbons to producing wells. An additional 10-50% of OOIP can be produced through tertiary recovery processes in addition to the oil produced during primary recovery.

While surfactants can be used as wetting agents, emulsifiers, detergents and solubilizers, they are also utilized in various stages of hydrocarbon recovery and processing, such as in drilling operations (e.g., drilling fluids/dispersants), reservoir injection (e.g., fracturing fluids, enhanced oil recovery fluids), well productivity (e.g., acidizing fluids), hydrocarbon transportation, environmental remediation, or a combination thereof.

Alkylaryl carboxylates have been used as enhanced oil recovery surfactants, such as described in U.S. Pat. No. 6,269,881, incorporated herein in full by reference, with one carboxylate group. There is a need for improved additive compositions for use in EOR applications.

SUMMARY

One embodiment of the disclosures is a method of enhancing oil recovery in a subterranean reservoir comprising: a) receiving a composition comprising a multicarboxylate, wherein the multicarboxylate comprises a compound comprising the chemical formula: $R_1$—$R_2$—$R_3$, wherein $R_1$ comprises a branched or unbranched, saturated or unsaturated, cyclic or non-cyclic, hydrophobic carbon chain having 7-150 carbon atoms; an oxygen atom linking $R_1$ and $R_2$; $R_2$ comprises an alkoxylated chain comprising ethylene oxide, propylene oxide, butylene oxide, or a combination thereof; and $R_3$ comprises a branched or unbranched hydrocarbon chain comprising 2-12 carbon atoms and 2-5 —COOH or —COOM groups wherein M is a monovalent, divalent, or trivalent cation; b) injecting the composition into the subterranean reservoir. In embodiments, $R_3$ comprises 2 carboxylate groups, and in other embodiments, $R_3$ comprises 3 carboxylate groups. In embodiments, $R_1$ comprises 13-130, 15-100, 18-90, 20-80, or 12-36 carbon atoms. In some embodiments $R_2$ comprises between 8-190, 10-170, 15-150, 20-60, or 15-90 oxide groups. Additionally, $R_2$ may comprise between 0-80 EO groups, 0-80 PO groups, and 0-80 BO groups. The composition may additionally comprise a polymer and/or an alkali metal. In embodiments, oil is produced from the subterranean reservoir. In some embodiments of the disclosures, the composition comprises between 0.3-20% of the multicarboxylate. In one embodiment, the multicarboxylate is used in amounts sufficient to recover additional oil from the subterranean reservoir.

Another embodiment of the disclosures is a method of enhancing oil recovery in a subterranean reservoir comprising: a) receiving a composition comprising a multicarboxylate, wherein the multicarboxylate comprises a compound comprising the chemical formula: $R_1$—$R_2$-$R_3$ wherein $R_1$ comprises a branched or unbranched, saturated or unsaturated, hydrophobic carbon chain comprising 7-150 carbon atoms; an oxygen atom linking $R_1$ and $R_2$; $R_2$ comprises an aryl group; and $R_3$ comprises a branched or unbranched hydrocarbon chain comprising 2-4 carbon atoms and 2-3 —COOH, —COO$^-$, or —COOM groups wherein M is a monovalent, divalent, or trivalent cation; b) injecting the composition into the subterranean reservoir. In embodiments, $R_3$ comprises 2 carboxylate groups, and in other embodiments, $R_3$ comprises 3 carboxylate groups. In embodiments, $R_1$ comprises 13-130, 15-100, 18-90, or 20-80, 12-36 carbon atoms. In some embodiments $R_2$ comprises a phenyl group. In some embodiments $R_2$ consists of a phenyl group. In additional embodiments, $R_2$ comprises a phenyl group with 0-3 methyl and/or ethyl group substitutions on the aromatic ring, and in some embodiments $R_2$ consists of a phenyl group with 0-3 methyl and/or ethyl group substitutions on the aromatic ring. In one embodiment, $R_1$ comprises a Guerbet alcohol. M may be Na, K, $NH_4$, Ca, Mg, Ba, or a water-soluble cationic counter-ion such as monoethanol amine, diethanol amine or triethanolamine. The composition of the method may additionally comprise a polymer and/or an alkali metal. In embodiments, oil is produced from the subterranean reservoir. In some embodiments of the disclosures, the composition comprises between 0.3-20% of the multicarboxylate. In one embodiment, the multicarboxylate is used in amounts sufficient to recover additional oil from the subterranean reservoir.

In another illustrative embodiment, the composition is prepared or employed in enhanced recovery at a temperature of 70° C. or greater.

In one embodiment, a method of enhancing oil recovery in a subterranean reservoir is provided, which includes providing the polymer flood composition, injecting the composition into the subterranean reservoir and producing oil therefrom.

DETAILED DESCRIPTION

Figure 1:
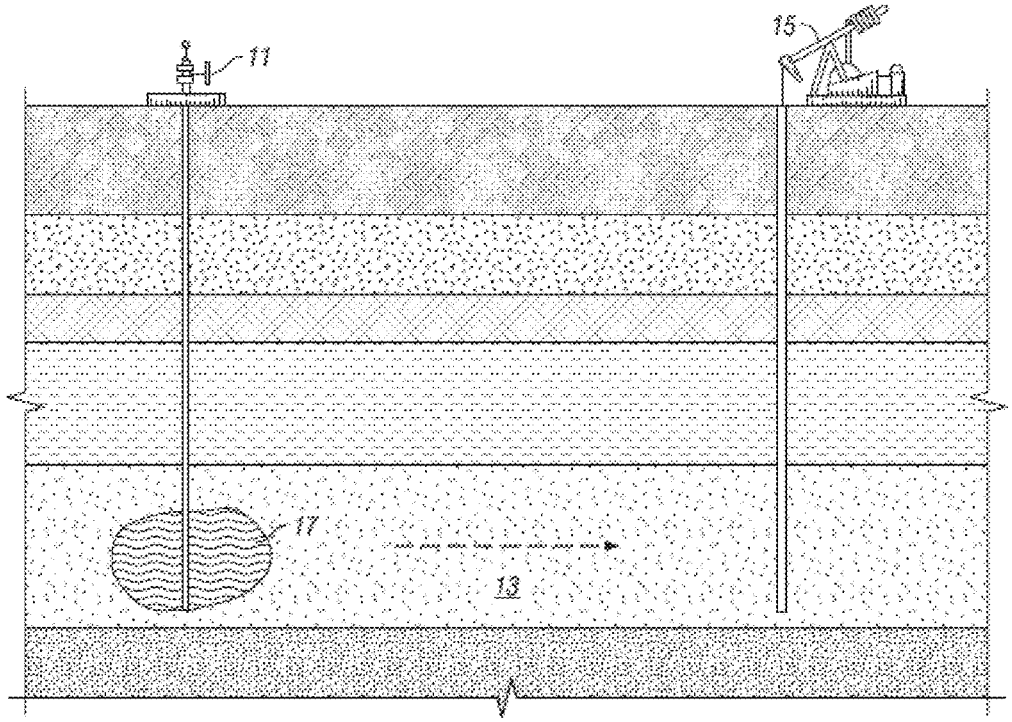
FIG. 1 is an illustration of surfactant-polymer slug entering a subterranean reservoir.

Embodiments of the disclosure relate to an alkoxy multicarboxylate compound and a method of making the alkoxy multicarboxylate. In certain aspects of the disclosure, the alkoxy multicarboxylate is used in a chemically enhanced oil recovery process.

As used herein, the term "equal" refers to equal values or values within the standard of error of measuring such values. The term "substantially equal" refers to an amount that is within 3% of the value recited. The term "about" refers to an amount that is within 10% of the value recited.

As used herein, "a" or "an" means "at least one" or "one or more" unless otherwise indicated. As used herein "multi-" or "plurality" refers to 2 or more.

Use of broader terms such as comprises, includes, having, etc. should be understood to provide support for narrower terms such as consisting of, consisting essentially of, comprised substantially of, etc.

"Effective amount," when used in reference to surfactant, refers to an amount sufficient to effect an increase in oil recovery over not including the component. For example, an effective amount of surfactant in a surfactant-polymer (SP) slug would increase oil recovery over only using the equivalent polymer slug without surfactant.

"Pore volume" or "PV" fraction as used herein refers to the total volume of pore space in the oil reservoir that is contemplated in a sweep (contacted pore space at ASP, AP, PD mobility ratio).

"Slug," as used herein, refers to an amount of a composition that is to be injected into a subterranean reservoir.

"Surfactant" refers to a compound which comprises at least one hydrophilic group and at least one hydrophobic group.

"Carboxylate surfactant", as used herein, refers to one of an alkoxy dicarboxylate, an alkoxy multicarboxylate, an alkylaryl multicarboxylate, or a combination.

"Divalent cation", as used herein, refers to IIA metals of the Periodic Table, including magnesium (Mg), calcium (Ca), and barium (Ba). Where an amount of divalent cation, in an aqueous solution, for example, is given in a percentage concentration, such as wt. %, the concentration of divalent cation is based on the weight of the cation in relation to the total weight of the composition of which the cation is a part.

"Turbidity" refers to the suspension of precipitates that do not readily settle out of solution and can result in a "cloudiness." Turbidity is determined by a Nepholometer that measures the relative amount of light able to pass through a solution. Turbidity is reported as NTU (Nephelometric Turbidity Units).

A "stable polymer composition" or "stable polymer suspension" as used herein refers to a composition comprising a polymer such as polyacrylamide (PAM) or partially hydrolyzed polyacrylamide (PHPA) suspension which does not undergo substantial settling after the polymer has been suspended in water for a period of at least 2 hours, and where the viscosity of the top, middle and bottom of the polymer suspension in a container (e.g., a mixer or holding tank, or a beaker) varies less 15%. The stability of the polymer suspension can be evaluated by visual observation over time, or qualitatively by methods known in the art including light scattering and turbidity methods, for changes in turbidity of more than 25% over a period of at least 4 hours.

Alkoxy Multicarboxylates: In general embodiments of the disclosure, the multicarboxylate compound is an alkoxy multicarboxylate having the chemical formula: $R_1$—$R_2$—$R_3$, wherein $R_1$ comprises a branched or unbranched, saturated or unsaturated, cyclic or non-cyclic, hydrophobic carbon chain having 7-150 carbon atoms; an oxygen atom linking $R_1$ and $R_2$; $R_2$ is an alkoxylated chain comprising alkoxy groups selected from EO (ethylene oxide), PO (propylene oxide), BO (butylene oxide), or a combination thereof; and $R_3$ comprises a branched or unbranched hydrocarbon chain comprising 2-12 carbon atoms and at least two carboxylate groups. In the acid form, the carboxylate group has the molecular formula —COOH; in ionic form, —COO—; in salt form, —COOM, where M represents a cation selected from monovalent, divalent, and trivalent cations. In one embodiment, M is selected from Na, K, NH4, Ca, Mg, Ba, and combinations. In another embodiment, M is a water-soluble cationic counter-ion such as monoethanol amine, diethanol amine or triethanolamine. As used herein, "multicarboxylate" refers to a multicarboxylate wherein $R_3$ contains two or more (e.g. 2-5) COOH or —COOM carboxylate groups. In one embodiment, the alkoxy multicarboxylate is an alkoxy dicarboxylate having 2 —COOH or —COOM groups wherein M is a monovalent, divalent, or trivalent cation. In one embodiment, the alkoxy multicarboxylate is an alkoxy tricarboxylate having 3 —COOH or —COOM groups. In one embodiment, the alkoxy multicarboxylate is an alkoxy tetracarboxylate having 4 —COOH or —COOM groups.

In one embodiment, $R_1$ comprises 7-150 carbon atoms, and in specific embodiments comprises 13-130, 15-100, 18-90, 20-80, or 12-36 carbon atoms. An oxygen atom links $R_1$ and $R_2$. In one embodiment $R_2$ comprises 0-80 ethylene oxide groups, 0-80 propylene oxide groups, 0-80 butylene oxide groups, or combinations thereof. In one embodiment, $R_2$ comprises 8-190, 5-80, 10-150, 15-100, 15-90, 10-60, 15-50, 20-30, or 2-30 alkoxy groups selected from EO, PO, BO and combinations thereof, in any order. Illustrative, non-limiting multicarboxylate compounds include $R_1$—$(BO)_{10}$—$(PO)_{14}$-$(EO)_{15}$—$R_3$ or $R_1$—$(PO)_{14}$-$(EO)_{15}$—$R_3$ or $R_1$—$(BO)_{10}$—$(PO)_{14}$—$(BO)_{10}$-$(EO)_{15}$—$R_3$. $R_3$ contains at least two carboxylate groups.

The following formulae illustrate three members of the family of carboxylates.

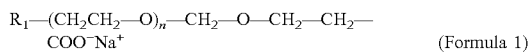

(Formula 1)

The above illustrates the molecular formula of a carboxylate with a single carboxylate (—COOM) group. In this example, the carboxylate group is associated with a cation M, where M is $Na^+$. $R_1$ in Formula 1 may be any one of a branched or unbranched, saturated or unsaturated, cyclic or non-cyclic, hydrophobic carbon chain having 7-150 carbon atoms. An oxygen atom links $R_1$ and $R_2$. $R_2$ as illustrated in Formula 1 is a polymeric chain of ethylene oxide (EO) groups, wherein n is the number of EO groups, and can range between 2 and 40. In one embodiment, n=2; in another embodiment, n=12; in another embodiment, n=20.

The following formula illustrates the molecular formula of a dicarboxylate, having two carboxylate (—COOM) groups, with M representing the cation $Na^+$.

Formula 2

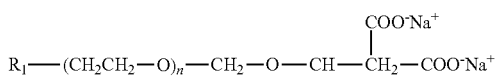

As in Formula 1, $R_2$ is a polymeric chain of ethylene oxide (EO) groups, wherein n is the number of EO groups, and can range between 2 and 40.

Formula 3 illustrates the molecular formula of a tricarboxylate, having three carboxylate (—COOM) groups, with M representing the cation Nat Formula 3

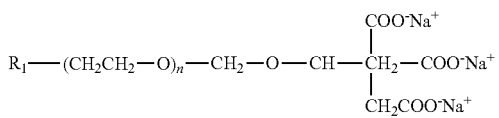

As in Formula 1, $R_2$ is a polymeric chain of ethylene oxide (EO) groups, wherein n is the number of EO groups, and can range between 2 and 40.

Other representative formulae of embodiments of the multicarboxylate additive are shown below:

Formula 4

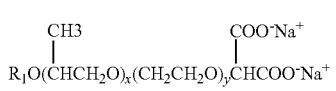

Formula 5

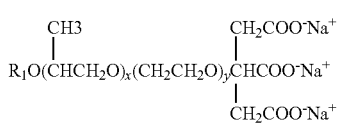

The alkoxy multicarboxylate may be a pure chemical or may be a mixture of different alkoxy multicarboxylates. In some embodiments, the alkoxy multicarboxylate is between 3,000-35,000 g/mol. In specific embodiments, the alkoxy multicarboxylate is between 10,000-25,000 g/mol or 12,000-20,000 g/mol.

Alkylaryl Multicarboxylate: In one embodiment, the multicarboxylate compound is an alkylaryl multicarboxylate compound having the chemical formula: $R_1$—$R_2$—$R_3$, wherein $R_1$ comprises a branched or unbranched, saturated or unsaturated, hydrophobic carbon chain comprising 7-150 carbon atoms; an oxygen atom linking $R_1$ and $R_2$; $R_2$ comprises an aryl group; and $R_3$ comprises a branched or unbranched hydrocarbon chain comprising 2-12 carbon atoms and 2-4 —COOH, —COO⁻, or —COOM groups wherein M is a monovalent, divalent, or trivalent cation.

In one embodiment, $R_1$ comprises 7-150 carbon atoms, and in specific embodiments comprises 13-130, 15-100, 18-90, 20-80, or 12-36 carbon atoms. In this embodiment, $R_2$ comprises a phenyl group having 0-3 methyl and/or ethyl group substitutions on the aromatic ring. $R_3$ comprises a branched or unbranched hydrocarbon chain having 2-4 carbon atoms and 2-3 carboxylate groups. Each carboxylate group can be located on any of the carbons on this carbon chain.

In some embodiments the alkylaryl multicarboxylate is between 3,000-35,000 g/mol. In specific embodiments, the alkylaryl multicarboxylate is between 10,000-25,000 g/mol or 12,000-20,000 g/mol.

Uses: Compositions of the disclosure can be used as wetting agents, oil additives, lubricants, emulsifiers, detergents, cosmetics, stabilizers, and solubilizers. They may also be utilized in various stages of hydrocarbon recovery and processing, such as in drilling operations (e.g., drilling fluids/dispersants), reservoir injection (e.g., fracturing fluids, recovery fluids), well productivity (e.g., acidizing fluids), hydrocarbon transportation, environmental remediation, polymer damage remediation, or a combination thereof.

Chemically Enhanced Oil Recovery Methods: As used herein and unless indicated otherwise, "multicarboxylate" refers to both alkoxy multicarboxylate and alkylaryl multicarboxylate. In one embodiment, the multicarboxylate composition is used as a surfactant in a chemically enhanced oil recovery (CEOR) process. In another embodiment, the multicarboxylate additive functions as a stabilizer in a CEOR process.

In one embodiment, the multicarboxylate composition functions as a stabilizer in polymer flooding with brine solutions containing a high concentration of divalent cations, e.g., greater than 500 ppm, and for temperatures greater than 70° C., even when employed in an amount less than 2000 ppm (0.2%). In another embodiment a stabilizer, the multicarboxylate is used in an amount ranging from 200 ppm (0.02%) to 1500 ppm (0.15%). Polymer flooding refers to injection streams containing any of associative polymers, water soluble unhydrolyzed polyacrylamides, or partially hydrolyzed polyacrylamides (PHPA) and with very little if any surfactant (<100 ppm). Polymer flooding can be by itself (e.g., alkaline polymer slug or AP slug), or as part of sequence of a polymer flooding slug followed by, or following, a polymer surfactant flooding (e.g., alkaline surfactant polymer or ASP slug). The polymer forms precipitates in hard brine and at temperatures >70° C., thereby limiting the application of polyacrylamides in polymer flooding at moderately high temperatures and hard brines due to plugging of the formation. Hard brines are defined as solutions containing >500 ppm of divalent ions. The only method to deploy PHPA under conditions of up to 100° C. is to remove divalent ions content. The use of the multicarboxylate composition as a stabilizer obviates the formation of precipitates in the injection stream, e.g., for the injection stream to have an NTU<20.

In one embodiment for use as a surfactant, the aqueous stream composition comprises 0.3-10% by weight of the multicarboxylate. In another embodiment, the CEOR composition comprises 0.5% to 5% by weight of the multicarboxylate as a surfactant. In yet another embodiment, the CEOR composition comprises 0.01% to 20% by weight of the multicarboxylate as a surfactant. In yet another embodiment, the CEOR composition comprises less than 1% by weight of the multicarboxylate as a surfactant.

The alkoxy carboxylate composition is suitable for CEOR composition when used in high temperature reservoirs, such as reservoirs above 55° C. The alkoxy carboxylate composition can be tailored to the conditions of the reservoir needing enhanced oil recovery. For example, the compound or the amount of the compound can be adjusted depending on the type of reservoir or the polymer used for the EOR application. In one embodiment, the length and branching of the alcohol portion can be decreased or increased, the length and ratio of each BO, EO, PO portions can be decreased or increased, and the length and positioning of the carboxylate surfactant portion may also be increased or decreased depending on the reservoir properties. In another embodiment, the components EO's (CH2-CH2-O) and PO's (CH(CH3)-CH2-O can be varied depending on the polymer selected for the injection stream.

FIG. 1 is an example oil recovery system which includes injection well 11 which extends to a portion of a subsurface reservoir 13 containing hydrocarbons for production, such that injection well 11 is in fluid communication with subsurface reservoir 13 and the hydrocarbons. Production well 15 is also in fluid communication with reservoir 13 in order to receive the hydrocarbons. Production well 15 is positioned a lateral distance away from injection well 11. For example, production well 15 can be positioned between 50 feet to 10,000 feet away from injection well 11. There can be additional production wells (not shown) at predetermined locations to optimally receive the hydrocarbons being pushed through reservoir 13 due to injections from additional injection wells (not shown).

In an embodiment, as illustrated in FIG. 1, a first surfactant-polymer (SP) slug 17 is injected through the injection well 11 into reservoir 13. The first SP slug 17 may be preceded by a pre-flush, such as a pre-flush of softened water at any desired salinity and/or by a polymer flood. As described further below, the SP slug comprises at least a carboxylate surfactant. The first SP slug 17 disperses through reservoir 13, with at least a portion thereof proceeding toward production well 15.

Figure 2:
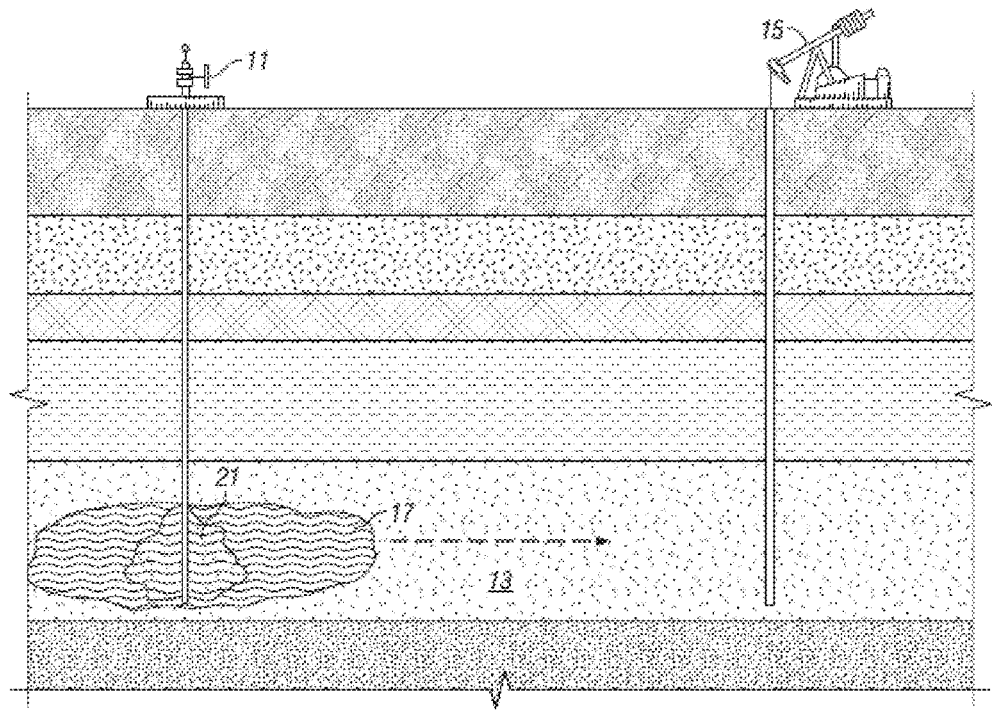
FIG. 2 is an illustration of a drive slug entering a subterranean reservoir following a surfactant-polymer slug.

A driver, chaser, or polymer drive slug 21 may be injected through the injection well into the reservoir after the SP slug 17, as illustrated in FIG. 2. The polymer used in the chaser slug 21 can be the same polymer used in the SP slug or may be different. In one embodiment, multiple chaser slugs can be injected. For example, a first chaser slug containing a small amount of polymer can be injected and the followed by a second chaser slug containing a larger amount of polymer.

For each reservoir operation, the optimal slug volumes may be determined prior to injection. For example, the SP slugs may be injected into the reservoir in volumes of between 0.05 to 0.5 PV, 0.1 to 0.4 PV, or about 0.1 PV. The necessary slug size can be determined through core flooding experiments and simulation. The volume of SP slug 17 may be the equal to, or different from the volume of the chaser. The speed of injection of the slugs may also vary depending on the reservoir operations.

The methods of the disclosure may be performed on-shore or off-shore, and may be adjusted to make the most efficient use of the location. As an example, seawater may be used as an aqueous base for any of the slugs described here, since off-shore production facilities tend to have an abundance of seawater available, limited storage space, and transportation costs to and from off-shore site are typically high. If seawater is used as the aqueous base, it can be softened prior to the addition of the alkali, polymer and/or surfactant, thereby removing any multivalent ions, specifically Mg and Ca. Additionally, the alkali, polymer, and surfactants may be added to an aqueous base fluid in a solid form or in a solution. Solid forms may be put into solution prior to addition to the production fluid or the solid form may be directly added to the production fluid.

Embodiments of the disclosure can be practiced in high temperature reservoirs, for example, greater than 50° C., greater than 55° C., greater than 60° C., greater than 65° C., greater than 70° C., greater than 80° C., or greater than 90° C. In some embodiments, the temperature of the reservoir is 15° C. to over 100° C.

Polymer: At least one polymer may be included with the multicarboxylate additive in the CEOR composition, to control the mobility of the CEOR composition when injected into a reservoir for enhanced oil recovery. Suitable polymers include, but are not limited to, biopolymers such as xanthan gum and scleroglucan and synthetic polymers such as water soluble unhydrolyzed or partially hydrolyzed polyacrylamides (HPAMs or PHPAs) and hydrophobically-modified associative polymers (APs). Also included are co-polymers of polyacrylamide (PAM) and one or both of 2-acrylamido 2-methylpropane sulfonic acid (and/or sodium salt) sold under the trademark AMPS (also more generally known as acrylamido tertiobutyl sulfonic acid or ATBS) and N-vinyl pyrrolidone (NVP). Molecular weights (Mw) of the polymers range from about 100,000 Daltons to about 30,000,000 Daltons, such as about 100,000 to about 500,000, or about 1,000,000 to about 20,000,000 Daltons. In specific embodiments of the disclosure the polymer is about 2,000,000 Daltons, about 8,000,000 Daltons, or about 20,000,000 Daltons. The polymer and the size of the polymer may be tailored to the permeability, temperature and salinity of the reservoir.

When the CEOR composition is injected as a slug into a subterranean reservoir, effective amounts of polymer are concentrations that allow the slug to efficiently sweep the reservoir. The required viscosity is a function of mobility ratio. Mobility ratio (M) is defined as water (or ASP) relative permeability divided by oil relative permeability multiplied by oil viscosity divided by water (or ASP) viscosity (krw/kro*μo/μw). Generally, a unit mobility ratio, M=1, or lower is desired in an ASP flood. In one example, the effective amount of polymer added to each slug is sufficient to reduce the viscosity of each subsequent slug, in order obtain favorable mobility ratio throughout the entire flood process. For example, effective amounts of polymer include, but are not limited to about 250 ppm to about 5,000 ppm, such as about 500 to about 2500 ppm concentration, or about 750 to 3000 ppm in order to achieve a favorable mobility ratio under the reservoir conditions of temperature. Different slugs may comprise different amounts of polymer.

Optional Surfactant: Surfactants may be included in the CEOR composition, along with the multicarboxylate additive, to lower the interfacial tension between the oil and water phase to less than about 0.01 dyne/cm (for example) and thereby recover additional oil by mobilizing and solubilizing oil trapped by capillary forces.

In one embodiment, an SP slug is prepared by combining a polymer with a multicarboxylate additive and 0.1-15% by weight of at least a surfactant that is not a multicarboxylate. Examples of surfactants that can be utilized include, but are not limited to, anionic surfactants, cationic surfactants, amphoteric surfactants, non-ionic surfactants, or a combination thereof. Anionic surfactants can include sulfates, sulfonates, phosphates, or other carboxylates. Such anionic surfactants are known and described in the art in, for example, U.S. Pat. No. 7,770,641, which is incorporated herein by reference. Examples of specific anionic surfactants include internal olefin sulfonates, isomerized olefin sulfonates, alkyl aryl sulfonates, medium alcohol ($C_{10}$ to $C_{36}$) alkoxy sulfates, alcohol ether [alkoxy] single carboxylates, and alcohol ether [alkoxy]sulfates. Example cationic surfactants include primary, secondary, or tertiary amines, or quaternary ammonium cations. Example amphoteric surfactants include cationic surfactants that are linked to a terminal sulfonate or carboxylate group. Example non-ionic surfactants include other alcohol alkoxylates such as alkylaryl alkoxy alcohols or alkyl alkoxy alcohols. Other non-ionic surfactants can include alkyl alkoxylated esters and alkyl polyglycosides. In some embodiments, multiple non-ionic surfactants such as non-ionic alcohols or non-ionic esters are combined. As a skilled artisan may appreciate, the surfactant(s) selection may vary depending upon such factors as salinity, temperature, and clay content in the reservoir. The surfactants can be injected in any manner such as continuously or in a batch process.

Alkali Additives: Depending on the type of reservoir, alkali may be included in the SP flood, making it an alkali-surfactant-polymer (ASP) flood. In one embodiment, the alkali employed is a basic salt of an alkali metal from Group IA metals of the Periodic Table, such as an alkali metal hydroxide, carbonate or bicarbonate. In one embodiment, the alkali is selected from the group consisting of sodium carbonate, sodium bicarbonate, sodium silicate, tetrasodium EDTA, sodium metaborate, sodium citrate, and sodium tetraborate. The alkali may be used in amounts ranging from about 0.3 to about 5 weight percent of the solution, such as about 0.5 to about 3 weight percent. As previously discussed, use of the alkali maintains surfactant in a high pH environment, which can minimize surfactant adsorption. Alkali can also protect the surfactant from hardness. Using alkali before and after an ASP slug can help to minimize surfactant adsorption, as a high pH environment is maintained through any diffusion of an ASP slug.

Additional Additives: The CEOR composition may also include additional additives, such as chelators, co-solvents, reducing agents/oxygen scavengers, and biocides. Chelators may be used to complex with multivalent cations and soften the water in the solution. Examples of chelators include ethylenediaminetetraacetic acid (EDTA) which can also be used as an alkali, methylglycinediacetic acid (MGDA). Chelants may be utilized to handle hard brines. The amount of chelant may be selected based on the amount of divalent ions in the slug solutions. For example, chelating agents can be used a 10:1 molar ratio with divalent cations such as calcium or magnesium or barium. Other chelating agents may work depending on the brine composition and the desired pH.

Suitable co-solvents may be selected from lower carbon chain alcohols like isopropyl alcohol, ethanol, n-propyl alcohol, n-butyl alcohol, sec-butyl alcohol, n-amyl alcohol, secamyl alcohol, n-hexyl alcohol, sec-hexyl alcohol and the like; alcohol ethers, polyalkylene alcohol ethers, polyalkylene glycols, poly(oxyalkylene)glycols, poly(oxyalkylene) glycols ethers or any other common organic co-solvent or combinations of any two or more co-solvents. For example, in an embodiment, an ether, ethylene glycol butyl ether (EGBE), is used and may be about 0.75 to 1.5 times the concentration of surfactant of ASP slug 21. Co-solvents, when used, may be present in an amount of about 0.5 to about 6.0 weight percent of the solution, such as from about 0.5 to about 4.0 weight percent, or about 0.5 to about 3 weight percent.

Reducing agents/oxygen scavengers such as sodium dithionite may be used to remove any oxygen in the mixture and reduce any free iron into $Fe^{2+}$. They can be used to protect synthetic polymers from reactions that cleave the polymer molecule and lower or remove viscosifying abilities. A reduced environment can also lower surfactant adsorption.

Biocides can be used to prevent organic (algal) growth in facilities, stop sulfate reducing bacteria (SRB) growth which "sour" the reservoir by producing dangerous and deadly $H_2S$, and are also used to protect biopolymers from biological life which feed on their sugar-like structures and therefore remove mobility control. Biocides include aldehydes and quaternary ammonium compounds.

EXAMPLES

The following illustrative examples are intended to be non-limiting.

Example 1

Alkoxy Dicarboxylate Synthesis

An alkoxy dicarboxylate is prepared using a two-step procedure. A sodium chloro acid salt is synthesized from a chloro acid compound comprising two carboxylates, such as a succinate. This reaction is conducted in a separate glass vessel with the product dried prior to addition to the surfactant step. The sodium chloro acetate group is then added to the alkyl alkoxy alcohol. This step synthesizes the alkoxy dicarboxylate surfactants. The process involves reacting alkyl alkoxy alcohols, for example, with a strong base to generate an anion on the alkoxy alcohol (loss of $H^+$ to strong base) which then displaces the chloride group from the added sodium chloro carboxylic salt to insert the carboxylate groups on to the alkoxy alcohol. The chemical mechanism for the reaction is an SN2 displacement. The reaction operating conditions range from room temperature to 150° C. at from 0 to 10 inches of mercury vacuum. The reactor for the second step has electronic controls for temperature and vacuum control with manual valves for gas blanketing. The reactants are charged to the reactor prior to heating. A cold trap is used to collect the tertiary butanol that is formed by the strong base as well as solvents to keep the reactants in solution. All electrical equipment is plugged into a temperature controller that is powered by a hood receptacle. The vacuum is controlled by a vacuum system monitor.

Example 2

Alkoxy Dicarboxylate Synthesis

In this example, 1.1 moles of potassium tert-butoxide is reacted with 1 mole of alkyl ethoxylate propoxylate $C_{10-18}$ alcohol at 45° C. for 1 hour while stirring at reduced pressure of 17 mm Hg. Tertiary butanol that is pulled off is collected in a dry ice/acetone trap. Then, 1.1 moles of sodium chlorosuccinate dissolved in 100 mL DMSO is added to the alkyl ethoxylate propoxylate $C_{10-18}$ alcohol/potassium t-butoxide mixture. The reaction temperature is increased to 90° C. and the pressure again reduced to about 17 mm Hg. The reaction mixture is stirred under these conditions over night or until liquid is no longer being collected in the dry ice/acetone mixture. The alkyl ethoxy propoxy succinate is isolated by ether and water extraction. The % conversion is greater than 90%.

Example 3

Alkoxy Multicarboxylate Synthesis

An alkoxy multicarboxylate is prepared using a two-step procedure. A sodium chloro multi-acid salt reagent is synthesized from a chloro acid compound. This reaction is conducted in a separate glass vessel with the product dried prior to addition to the surfactant step. A sodium chloro multicarboxylate group is then added to the alkyl alkoxy alcohol. This step synthesizes the alkoxy multicarboxylate surfactants. The process involves reacting alkyl alkoxy alcohols with a strong base to generate an anion on the alkoxy alcohol (loss of $H^+$ to strong base) which then displaces the chloride group from the added sodium chloro multicarboxylic salt to insert the carboxylate groups. The chemical mechanism for the reaction is an SN2 displacement. The reaction operating conditions ranges from room temperature to 150° C. at from 0 to 10 inches of mercury vacuum. The reactor for the second step has electronic controls for temperature and vacuum control with manual valves for gas blanketing. The reactants are then charged to the reactor prior to heating. A cold trap is used to collect the tertiary butanol that is formed by the strong base as well as solvents to keep the reactants in solution. All electrical equipment is plugged into a temperature controller that is powered by a hood receptacle. The vacuum is controlled by a vacuum system monitor.

Example 4

Alkoxy Tricarboxylate Synthesis

In this example, 1.1 moles of potassium tert-butoxide is reacted with 1 mole of alkyl ethoxylate propoxylate $C_{10-18}$ alcohol at 45° C. for 1 hour while stirring at reduced pressure of 17 mm Hg. Tertiary butanol that is pulled off is collected in a dry ice/acetone trap. Then, 1.1 moles of sodium chloro 1,2,3-propanetricarboxylate dissolved in 100 mL DMSO is added to the alkyl ethoxylate propoxylate $C_{10-18}$ alcohol/potassium t-butoxide mixture. The reaction temperature is increased to 90° C. and the pressure again reduced to about 17 mm Hg. The reaction mixture is stirred under these conditions over night or until liquid is no longer being collected in the dry ice/acetone mixture. The alkyl ethoxy propoxy tricarboxylate is isolated by ether and water extraction. The % conversion is greater than 90%.

Example 5

Alkoxy Tetracarboxylate Synthesis

In this example, 1.1 moles of potassium tert-butoxide is reacted with 1 mole of alkyl ethoxylate propoxylate C10-18 alcohol at 45° C. for 1 hour while stirring at reduced pressure of 17 mm Hg. Tertiary butanol that is pulled off is collected in a dry ice/acetone trap. Then, 1.1 moles of sodium chloro 1,1,2,3-propanetetracarboxylate dissolved in 100 mL DMSO is added to the alkyl ethoxylate propoxylate C10-18 alcohol/potassium t-butoxide mixture. The reaction temperature is increased to 90° C. and the pressure again reduced to about 17 mm Hg. The reaction mixture is stirred under these conditions over night or until liquid is no longer being collected in the dry ice/acetone mixture. The alkyl ethoxy propoxy tetracarboxylate is isolated by ether and water extraction. The % conversion is greater than 90%.

Example 6

Alkylaryl Multicarboxylate Synthesis

An alkylaryl multicarboxylate is synthesized as follows. A slight excess of (1.1 moles base: 1 mole of substituted phenol) potassium t-butoxide is reacted with a guerbet/phenol compound at about 45° C. under reduced pressure of 17 mm Hg for 2 hours. Tertiary butanol is removed and collected in a dry ice/isopropanol trap. Then a slight excess (1.1:1, for example) of chloro multicarboxylate (e.g. succinate) is added to the phenol mixture. The reaction temperature is increased to about 90° C. at a pressure of less than or equal to 17 mm Hg pressure overnight. The multicarboxylate material is separated by lowering the solution pH to about 3 with acid solution and heating the mixture to 90° C. The upper layer of the resulting mixture is collected. Changing the pH to about 8 with NaOH yields the salt form of the multicarboxylate.

Example 7

Analysis of Dicarboxylate

A sample of dicarboxylate was synthesized as described above. The product from the reaction of both chloro acetate or chloro succinate with a nonionic alkoxy alcohol yield products with either one (acetate) or two acid (succinate) terminal groups.

IR (4000-600 Wavenumbers transmittance): The acetate product has a broad carbonyl singlet shifted to lower wavenumbers indicating a lowering of bond strength. However, the succinate product has doublet carbonyl peak. One peak of the doublet is close to the starting chloro succinate while the second is at a lower wavenumber similar to the acetate product. The doublet may also indicate the proximity of the alkoxy groups to one acid group vs. the second or terminal acid group.

HPLC (Column: Zorbax SB-C8 4.6×250 mm, 5 um, Mobil Phase: 90% $H_2O$, 10% acetonitrile, 8 gm phosphorus acid, Detector: Agilent Diode Array Detector G4212A/B): The product from the chloro acetate reaction is shifted by 1.5 minutes to shorter retention on the column indicating less chromatographic separation with the polar mobile phase than the chloro acetate reactant. The chloro succinate product has a similar retention time to the acetate product due to the presence of the alkoxy groups which affects the chromatographic separation more than the addition of a second acid group. However, the product retention time is only 0.6 minutes shorter than the chloro succinate reactant indicating that the two acid groups are separated even less with the polar mobile phase.

Both the IR and HPLC results indicate that an alcohol alkoxylated dicarboxylate is synthesized using the described methods.

Example 8

Comparative Example

A solution of hard brine (containing >500 ppm) containing partially hydrolyzed polyacrylamide (PHPA) at a concentration of 2000 ppm and at a temperature of >70° C. is provided. It is observed that PHPA in the presence of >500 ppm divalent ions forms a solid precipitate (flocculates) in solution, with NTU>20. If this hard brine containing PHPA is used for in polymer flooding at moderately high temperatures, it is expected to plug the formation.

Example 9

Comparative Example

Example 8 is repeated except the PHPA concentration is 1000 ppm. It is observed that solid precipitate (flocculates) still forms in the solution, with NTU>20.

Example 10

Comparative Example

Example 8 is repeated, except that the divalent ions content is removed (to be less than 100 ppm) prior to the addition of PHPA. No precipitate is formed. NTU is <20.

Example 11

Addition of Stabilizer

Example 8 is repeated with field brines at 120° C. under anaerobic conditions (solutions degassed and sealed in glass ampoules) with several divalent chelating chemicals. No precipitation occurred (and NTU<20) with the addition of alkoxylated carboxylate as an additive for 9 hours at 120° C. The additive has a formula of R(28 carbons)-O—(CH2-CH2-O)25-COO—Na+. The concentrations of the surfactant were 0.15% (1500 ppm) and 0.05% (500 ppm). These surfactant concentrations are much lower than the same surfactant used in a surfactant oil flood which ranges from 1-2%.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items.

All citations referred herein are expressly incorporated herein by reference.

What is claimed is:

1. An aqueous stream for injecting into a subterranean reservoir for enhanced oil recovery applications, the aqueous stream having a composition comprising:
    a) 0.01-20% by weight of an additive compound comprising the chemical formula:

$R_1$—$R_2$—$R_3$, wherein:

$R_1$ comprises a branched or unbranched, saturated or unsaturated, cyclic or non-cyclic, hydrophobic carbon chain having 7-150 carbon atoms and an oxygen atom linking $R_1$ and $R_2$;

$R_2$ comprises an alkoxylated chain comprising at least one oxide group selected from the group consisting of ethylene oxide, propylene oxide, butylene oxide, and combinations thereof wherein $R_2$ is selected from the group consisting of —$(BO)_m$—$(PO)_n$-$(EO)_o$—, —$(BO)_p$—$(PO)_q$—$(BO)_r$-$(EO)_s$—, and —$(BO)_t$-$(EO)_u$—, wherein m through u≠0, m+n+o=8-190, p+q+r+s=8-190, and t+u=8-190; and $R_3$ consists of a branched or unbranched hydrocarbon chain comprising 2-12 carbon atoms and 2-5 —COOH or 2-5 —COOM groups wherein M is a monovalent, divalent, or trivalent cation;

b) 250 to 5000 ppm of a polymer selected from the group consisting of xanthan gum, scleroglucan, water soluble unhydrolyzed or partially hydrolyzed polyacrylamides, hydrophobically-modified associative polymers, co-polymers of polyacrylamide, 2-acrylamido 2-methylpropane sulfonic acid and its sodium salt, and N-vinyl pyrrolidone;

c) 0.3 to 20 weight percent of a basic salt of a Group IA alkali metal; and d) 0.5 to about 6.0 weight percent of a lower carbon chain alcohol co-solvent.

2. The aqueous stream of claim 1, wherein the aqueous stream is located in the subterranean reservoir.

3. The aqueous stream of claim 1, wherein:
    $R_1$ comprises 12-36 carbon atoms;
    $R_2$ comprises between 0-80 ethylene oxide groups, 0-80 propylene oxide groups, and 0-80 butylene oxide groups;
    $R_3$ comprises any of 2, 3, or 4 —COOH or 2, 3, or 4 —COOM groups; and
    M comprises Na, K, $NH_4$, Ca, Mg, or Ba.

4. The aqueous stream of claim 1, wherein:
    $R_1$ comprises 12-36 carbon atoms;
    $R_2$ comprises an aryl group;
    $R_3$ comprises any of 2, 3, or 4 —COOH or 2, 3, or 4 —COOM groups; and
    M comprises Na, K, $NH_4$, Ca, Mg, or Ba.

5. The aqueous stream of claim 1, wherein:
the polymer is selected from the group consisting of associative polymers, water soluble unhydrolyzed polyacrylamides, and partially hydrolyzed polyacrylamides;
the aqueous stream is injected into the reservoir at a temperature of at least 70° C.;
the aqueous stream has a concentration of divalent cations of at least 500 ppm;
and the additive compound is present in an amount ranging from 200 ppm (0.02%) to 1500 ppm (0.15%) such that the aqueous stream has a Nephlometric Turbidity Units value of less than 20.

6. The aqueous stream of claim 3, wherein the polymer is partially hydrolyzed polyacrylamide.

7. A method of enhancing oil recovery in a subterranean reservoir, comprising:
a) providing at least one injection/production well pair comprising an injection well and a production well in the subterranean reservoir;
b) injecting an aqueous stream via the injection well into the subterranean reservoir; and
c) recovering oil via the production well from the subterranean reservoir;
wherein the aqueous stream has a composition comprising:
  i. 0.01-20% by weight of an additive compound comprising the chemical formula:

$R_1$—$R_2$—$R_3$, wherein:

$R_1$ comprises a branched or unbranched, saturated or unsaturated, cyclic or non-cyclic, hydrophobic carbon chain having 7-150 carbon atoms and an oxygen atom linking $R_1$ and $R_2$;
    $R_2$ comprises an alkoxylated chain comprising at least one oxide group selected from the group consisting of ethylene oxide, propylene oxide, butylene oxide, and combinations thereof wherein $R_2$ is selected from the group consisting of —(BO)$_m$—(PO)$_n$-(EO)$_o$—, —(BO)$_p$—(PO)$_q$—(BO)$_r$-(EO)$_s$—, and —(BO)$_t$-(EO)$_u$—, wherein m through u≠0, m+n+o=8–190, p+q+r+s=8-190, and t+u=8-190; and
    $R_3$ consists of a branched or unbranched hydrocarbon chain comprising 2-12 carbon atoms and 2-5 —COOH or 2-5 —COOM groups wherein M is a monovalent, divalent, or trivalent cation;
  ii. 250 to 5000 ppm of a polymer selected from the group consisting of xanthan gum, scleroglucan, water soluble unhydrolyzed or partially hydrolyzed polyacrylamides, hydrophobically-modified associative polymers, co-polymers of polyacrylamide, 2-acrylamido 2-methylpropane sulfonic acid and its sodium salt, and N-vinyl pyrrolidone;
  iii. 0.3 to 20 weight percent of a basic salt of a Group IA alkali metal; and
  iv. 0.5 to about 6.0 weight percent of a lower carbon chain alcohol co-solvent.

8. The method of claim 7, wherein the additive compound is present in the aqueous stream in an amount ranging from 200 ppm (0.02%) to 1500 ppm (0.15%).

9. The method of claim 7, wherein:
$R_1$ comprises 12-36 carbon atoms;
$R_2$ comprises between 0-80 ethylene oxide groups, 0-80 propylene oxide groups, and 0-80 butylene oxide groups;
$R_3$ comprises any of 2, 3, or 4 —COOH or 2, 3, or 4 —COOM groups; and
M comprises Na, K, NH$_4$, Ca, Mg, or Ba.

10. The method of claim 7, wherein:
$R_1$ comprises 12-36 carbon atoms;
$R_2$ comprises an aryl group;
$R_3$ comprises any of 2, 3, or 4 —COOH or 2, 3, or 4 —COOM groups; and
M comprises Na, K, NH$_4$, Ca, Mg, or Ba.

* * * * *